United States Patent
Jia et al.

(10) Patent No.: US 9,351,872 B2
(45) Date of Patent: May 31, 2016

(54) ATTENUATED RF POWER FOR AUTOMATED CAPSULORHEXIS

(71) Applicant: Alcon Research, Ltd., Fort Worth, TX (US)

(72) Inventors: Guangyao Jia, Irvine, CA (US); Ahmad Salehi, Irvine, CA (US); Glenn Robert Sussman, Laguna Niguel, CA (US); Ann Yadlowsky, Sunnyvale, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 14/836,075

(22) Filed: Aug. 26, 2015

(65) Prior Publication Data

US 2015/0359671 A1   Dec. 17, 2015

Related U.S. Application Data (63) Continuation of application No. 12/893,149, filed on Sep. 29, 2010, now Pat. No. 9,149,388.

(51) Int. Cl.
| | |
|---|---|
| *A61F 9/007* | (2006.01) |
| *A61B 18/12* | (2006.01) |
| *A61B 18/00* | (2006.01) |
| *A61B 18/14* | (2006.01) |

(52) U.S. Cl.
CPC ... *A61F 9/00754* (2013.01); *A61B 2018/00321* (2013.01); *A61B 2018/00702* (2013.01); *A61B 2018/00726* (2013.01); *A61B 2018/1407* (2013.01)

(58) Field of Classification Search
CPC ........... A61B 2018/00321; A61B 2018/00702; A61B 2018/1407; A61B 2018/1412; A61B 18/12; A61F 9/007; A61F 9/0079
See application file for complete search history.

(56) References Cited

U.S. PATENT DOCUMENTS

| | | |
|---|---|---|
| 3,159,161 A | 12/1964 | Ness |
| 3,809,093 A | 5/1974 | Abraham |

(Continued)

FOREIGN PATENT DOCUMENTS

| | | |
|---|---|---|
| DE | 3038024 A1 | 4/1982 |
| DE | 3205959 A1 | 9/1983 |

(Continued)

OTHER PUBLICATIONS

Choi, B. et al., "Analysis of thermal relaxation during laser irradiation of tissue", Lasers in Surgery and Medicine, Nov. 2001, vol. 29, Issue 4, pp. 351-359.

(Continued)

*Primary Examiner* — Ronald Hupczey, Jr.
(74) *Attorney, Agent, or Firm* — Kenneth D. Bassinger (57) ABSTRACT

A capsulorhexis apparatus includes a capsulorhexis probe configured for insertion into an eye through an incision and a pulse generator configured to deliver at least one radio-frequency (RF) pulse to the capsulorhexis probe. The delivered RF pulse has a pre-determined attenuation profile such that the power level of the delivered RF pulse is substantially attenuated over the RF pulse's duration. In some embodiments, the pulse generator is configured to deliver a series of two or more RF pulses to the eye, such that the energy of each of the second and subsequent pulses of the series is substantially attenuated relative to the energy of the immediately preceding pulse.

12 Claims, 4 Drawing Sheets

(56) References Cited

U.S. PATENT DOCUMENTS

| | | | |
|---|---|---|---|
| 3,844,272 A | 10/1974 | Banko | |
| 3,897,787 A * | 8/1975 | Ikuno | A61B 18/16 361/86 |
| 3,915,172 A | 10/1975 | Wichterle et al. | |
| 3,949,750 A | 4/1976 | Freeman | |
| 4,002,169 A | 1/1977 | Cupler, II | |
| 4,026,295 A | 5/1977 | Lieberman | |
| 4,068,664 A | 1/1978 | Sharp et al. | |
| 4,210,146 A | 7/1980 | Banko | |
| 4,301,802 A | 11/1981 | Poler | |
| 4,367,744 A | 1/1983 | Sole | |
| 4,368,734 A | 1/1983 | Banko | |
| 4,429,694 A | 2/1984 | McGreevy | |
| 4,457,757 A | 7/1984 | Molteno | |
| 4,481,948 A | 11/1984 | Sole | |
| 4,510,274 A | 4/1985 | Okazaki et al. | |
| 4,530,356 A | 7/1985 | Helfgott et al. | |
| 4,530,359 A | 7/1985 | Helfgott et al. | |
| 4,531,934 A | 7/1985 | Kossovsky et al. | |
| 4,559,942 A | 12/1985 | Eisenberg | |
| 4,570,632 A | 2/1986 | Woods | |
| 4,607,622 A | 8/1986 | Fritch et al. | |
| 4,676,243 A | 6/1987 | Clayman | |
| 4,706,669 A | 11/1987 | Schlegel | |
| 4,708,138 A | 11/1987 | Pazandak | |
| 4,729,761 A | 3/1988 | White | |
| 4,766,896 A | 8/1988 | Pao | |
| 4,766,897 A | 8/1988 | Smirmaul | |
| 4,781,675 A | 11/1988 | White | |
| 4,805,616 A | 2/1989 | Pao | |
| 4,869,716 A | 9/1989 | Smirmaul | |
| 4,885,004 A | 12/1989 | Pao | |
| 4,900,300 A | 2/1990 | Lee | |
| 4,911,161 A | 3/1990 | Schechter | |
| 4,936,825 A | 6/1990 | Ungerleider | |
| 4,950,272 A | 8/1990 | Smirmaul | |
| 4,955,859 A | 9/1990 | Zilber | |
| 4,955,894 A | 9/1990 | Herman | |
| 4,986,825 A | 1/1991 | Bays et al. | |
| 4,994,066 A | 2/1991 | Voss | |
| 5,047,008 A | 9/1991 | de Juan, Jr. et al. | |
| 5,085,664 A | 2/1992 | Bozzo | |
| 5,123,906 A | 6/1992 | Kelman | |
| 5,135,530 A | 8/1992 | Lehmer | |
| 5,180,362 A | 1/1993 | Worst | |
| 5,188,634 A | 2/1993 | Hussein et al. | |
| 5,199,445 A | 4/1993 | Rubinfeld | |
| 5,203,865 A | 4/1993 | Siepser | |
| 5,234,436 A | 8/1993 | Eaton et al. | |
| 5,242,404 A | 9/1993 | Conley et al. | |
| 5,242,449 A | 9/1993 | Zaleski | |
| 5,261,923 A | 11/1993 | Soares | |
| 5,269,787 A | 12/1993 | Cozean, Jr. et al. | |
| 5,322,504 A | 6/1994 | Doherty et al. | |
| 5,342,377 A | 8/1994 | Lazerson | |
| 5,346,491 A | 9/1994 | Oertli | |
| 5,360,399 A | 11/1994 | Stegmann | |
| 5,364,405 A | 11/1994 | Zaleski | |
| 5,374,244 A | 12/1994 | Clement et al. | |
| 5,395,361 A | 3/1995 | Fox et al. | |
| 5,411,510 A | 5/1995 | Fugo | |
| 5,413,574 A | 5/1995 | Fugo | |
| 5,423,330 A | 6/1995 | Lee | |
| 5,423,841 A | 6/1995 | Kornefeld | |
| 5,439,474 A | 8/1995 | Li | |
| 5,445,637 A * | 8/1995 | Bretton | A61F 9/00736 604/22 |
| 5,466,234 A | 11/1995 | Loeb et al. | |
| 5,478,338 A | 12/1995 | Reynard | |
| 5,484,433 A | 1/1996 | Taylor et al. | |
| 5,486,165 A | 1/1996 | Stegmann | |
| 5,487,725 A | 1/1996 | Peyman | |
| 5,522,829 A | 6/1996 | Michalos | |
| 5,527,332 A | 6/1996 | Clement | |
| 5,562,692 A | 10/1996 | Bair | |
| 5,569,197 A | 10/1996 | Helmus et al. | |
| 5,569,280 A | 10/1996 | Kamerling | |
| 5,601,094 A | 2/1997 | Reiss | |
| 5,601,593 A | 2/1997 | Freitag | |
| 5,626,558 A | 5/1997 | Suson | |
| 5,630,827 A | 5/1997 | Vijfvinkel | |
| 5,651,783 A | 7/1997 | Reynard | |
| 5,662,670 A | 9/1997 | Michalos | |
| 5,669,923 A | 9/1997 | Gordon | |
| 5,670,161 A | 9/1997 | Healy | |
| 5,683,592 A | 11/1997 | Bartholomew et al. | |
| 5,700,243 A | 12/1997 | Narciso, Jr. | |
| 5,716,363 A | 2/1998 | Josephberg | |
| 5,728,117 A | 3/1998 | Lash | |
| 5,733,297 A | 3/1998 | Wang | |
| 5,741,244 A | 4/1998 | Klaas | |
| 5,755,731 A | 5/1998 | Grinberg | |
| 5,766,171 A | 6/1998 | Silvestrini | |
| 5,792,166 A | 8/1998 | Gordon et al. | |
| 5,827,321 A | 10/1998 | Roubin et al. | |
| 5,860,994 A | 1/1999 | Yaacobi | |
| 5,868,697 A | 2/1999 | Richter et al. | |
| 5,873,883 A | 2/1999 | Cozean, Jr. et al. | |
| 5,888,201 A | 3/1999 | Stinson et al. | |
| 5,891,084 A | 4/1999 | Lee | |
| 5,893,862 A | 4/1999 | Pratt et al. | |
| 5,898,697 A | 4/1999 | Hurme et al. | |
| 5,921,999 A | 7/1999 | Dileo | |
| 5,925,056 A | 7/1999 | Thomas et al. | |
| 5,957,921 A | 9/1999 | Mirhashemi et al. | |
| 5,989,262 A | 11/1999 | Josephberg | |
| 6,036,688 A | 3/2000 | Edwards | |
| 6,059,792 A | 5/2000 | Josephberg | |
| 6,066,138 A | 5/2000 | Sheffer et al. | |
| 6,135,998 A | 10/2000 | Palanker | |
| 6,142,996 A | 11/2000 | Mirhashemi et al. | |
| 6,162,202 A | 12/2000 | Sicurelli et al. | |
| 6,165,190 A | 12/2000 | Nguyen | |
| 6,179,830 B1 | 1/2001 | Kokubu | |
| 6,203,518 B1 | 3/2001 | Anis et al. | |
| 6,217,598 B1 | 4/2001 | Berman et al. | |
| 6,241,721 B1 | 6/2001 | Cozean et al. | |
| 6,264,668 B1 | 7/2001 | Prywes | |
| 6,306,155 B1 | 10/2001 | Chandler et al. | |
| 6,379,370 B1 | 4/2002 | Feinsod | |
| 6,413,262 B2 | 7/2002 | Saishin et al. | |
| 6,440,103 B1 | 8/2002 | Hood et al. | |
| 6,503,263 B2 | 1/2003 | Adams | |
| 6,506,176 B1 | 1/2003 | Mittelstein et al. | |
| 6,544,254 B1 | 4/2003 | Bath | |
| 6,551,326 B1 | 4/2003 | Van Heugten et al. | |
| 6,575,929 B2 | 6/2003 | Sussman et al. | |
| 6,616,996 B1 | 9/2003 | Keith et al. | |
| 6,629,980 B1 | 10/2003 | Eibschitz-Tsimhoni | |
| 6,673,064 B1 | 1/2004 | Rentrop | |
| 6,764,439 B2 | 7/2004 | Schaaf et al. | |
| 6,893,435 B2 * | 5/2005 | Goble | A61B 18/1445 606/34 |
| 6,966,927 B1 | 11/2005 | Silvestrini | |
| 6,979,328 B2 * | 12/2005 | Baerveldt | A61F 9/00781 128/849 |
| 7,011,666 B2 | 3/2006 | Feinsod | |
| 7,135,009 B2 | 11/2006 | Tu et al. | |
| 7,303,557 B2 * | 12/2007 | Wham | A61B 18/1442 606/34 |
| 7,824,870 B2 | 11/2010 | Kovalcheck et al. | |
| 8,137,344 B2 * | 3/2012 | Jia | A61B 18/14 606/45 |
| 8,157,797 B2 * | 4/2012 | Boukhny | A61F 9/00754 606/45 |
| 2002/0007150 A1 | 1/2002 | Johnson | |
| 2002/0091402 A1 | 7/2002 | Feinsod | |
| 2002/0161365 A1 | 10/2002 | Martins | |
| 2004/0092982 A1 | 5/2004 | Sheffer | |
| 2004/0106929 A1 | 6/2004 | Masket | |
| 2004/0116950 A1 | 6/2004 | Eibschitz-Tsimhoni | |
| 2005/0054972 A1 | 3/2005 | Adams et al. | |
| 2005/0228419 A1 | 10/2005 | El-Mansoury | |
| 2006/0036270 A1 | 2/2006 | Terao | |

(56) References Cited

U.S. PATENT DOCUMENTS

| | | | |
|---|---|---|---|
| 2006/0100617 A1* | 5/2006 | Boukhny | A61F 9/00754 606/41 |
| 2006/0106370 A1 | 5/2006 | Baerveldt et al. | |
| 2006/0241580 A1 | 10/2006 | Mittelstein et al. | |
| 2006/0259053 A1 | 11/2006 | El-Mansoury | |
| 2007/0010812 A1 | 1/2007 | Mittelstein et al. | |
| 2007/0049957 A1 | 3/2007 | Benitez et al. | |
| 2007/0060926 A1 | 3/2007 | Escaf | |
| 2007/0073275 A1 | 3/2007 | Conston et al. | |
| 2007/0078359 A1 | 4/2007 | Luloh et al. | |
| 2007/0156129 A1 | 7/2007 | Kovalcheck | |
| 2007/0191862 A1 | 8/2007 | Ellis | |
| 2007/0239156 A1 | 10/2007 | Palanker et al. | |
| 2007/0276420 A1 | 11/2007 | Sorensen et al. | |
| 2008/0188846 A1* | 8/2008 | Palanker | A61B 18/14 606/32 |
| 2008/0188849 A1 | 8/2008 | Goldberg et al. | |
| 2008/0262525 A1 | 10/2008 | Chang et al. | |
| 2009/0287143 A1 | 11/2009 | Line | |
| 2009/0287233 A1 | 11/2009 | Huculak | |
| 2010/0022943 A1 | 1/2010 | Mauch et al. | |
| 2010/0057069 A1 | 3/2010 | Ben-Nun | |
| 2010/0094278 A1 | 4/2010 | Jia et al. | |
| 2010/0145447 A1 | 6/2010 | Jia et al. | |
| 2010/0179544 A1 | 7/2010 | Boukhny et al. | |
| 2010/0312232 A1 | 12/2010 | Jia et al. | |
| 2010/0312252 A1 | 12/2010 | Jia et al. | |
| 2011/0118734 A1 | 5/2011 | Auld et al. | |
| 2011/0144641 A1* | 6/2011 | Dimalanta, Jr. | A61B 18/1477 606/45 |

FOREIGN PATENT DOCUMENTS

| | | |
|---|---|---|
| DE | 3248101 A1 | 6/1984 |
| DE | 3434930 A1 | 4/1986 |
| DE | 8710541 U1 | 11/1987 |
| DE | 4012882 A1 | 10/1991 |
| DE | 9311879 U1 | 11/1993 |
| DE | 19719549 A1 | 11/1998 |
| DE | 19740530 A1 | 3/1999 |
| DE | 19809510 A1 | 9/1999 |
| DE | 10220253 A1 | 11/2002 |
| EP | 0165657 B1 | 3/1985 |
| EP | 0136855 B1 | 4/1985 |
| EP | 0183385 B1 | 10/1985 |
| EP | 0358990 A1 | 8/1989 |
| EP | 0335714 A2 | 10/1989 |
| EP | 0228185 B1 | 7/1990 |
| EP | 0506618 B1 | 3/1992 |
| EP | 0506618 A1 | 9/1992 |
| EP | 0355341 B1 | 10/1992 |
| EP | 0537116 A1 | 4/1993 |
| EP | 0898947 A2 | 3/1999 |
| EP | 0730848 B1 | 4/2000 |
| EP | 1010410 A1 | 6/2000 |
| EP | 0986328 A4 | 5/2001 |
| EP | 1095641 A1 | 5/2001 |
| EP | 1809196 A4 | 3/2008 |
| ES | 2103635 | 9/1997 |
| FR | 2544979 A1 | 11/1984 |
| FR | 2588751 A1 | 4/1987 |
| FR | 2676355 | 11/1992 |
| FR | 2677244 A1 | 12/1992 |
| FR | 2702955 A1 | 9/1994 |
| FR | 2707872 A1 | 1/1995 |
| FR | 2710269 A1 | 3/1995 |
| FR | 2830186 A1 | 4/2003 |
| FR | 2855745 A1 | 12/2004 |
| FR | 2855746 A1 | 12/2004 |
| FR | 2924924 A1 | 6/2009 |
| GB | 2247174 A | 2/1992 |
| GB | 2437252 A | 10/2007 |
| JP | H576562 | 3/1993 |
| JP | 2002538881 T2 | 11/2002 |
| JP | 200761627 | 3/2007 |
| SU | 452338 | 12/1974 |
| SU | 1148613 A1 | 4/1985 |
| SU | 1301400 A1 | 4/1987 |
| SU | 1395314 A1 | 5/1988 |
| SU | 1431752 A1 | 10/1988 |
| SU | 1440496 A1 | 11/1988 |
| SU | 1766403 A1 | 10/1992 |
| SU | 1790934 A1 | 1/1993 |
| SU | 1790935 A1 | 1/1993 |
| SU | 1805938 A3 | 3/1993 |
| WO | 8602257 A1 | 4/1986 |
| WO | 9301755 A1 | 2/1993 |
| WO | 9320765 A1 | 10/1993 |
| WO | 9418920 A1 | 9/1994 |
| WO | 9508310 A1 | 3/1995 |
| WO | 9606570 A1 | 3/1996 |
| WO | 9726835 A1 | 7/1997 |
| WO | 9730669 A1 | 8/1997 |
| WO | 9849945 A1 | 11/1998 |
| WO | 9960936 A1 | 12/1999 |
| WO | 0048540 A1 | 8/2000 |
| WO | 0156519 A1 | 8/2001 |
| WO | 0160266 A1 | 8/2001 |
| WO | 0182796 A1 | 11/2001 |
| WO | 03022174 A2 | 3/2003 |
| WO | 03039335 A2 | 5/2003 |
| WO | 03045290 A1 | 6/2003 |
| WO | 2004039295 A1 | 5/2004 |
| WO | 2004071312 A1 | 8/2004 |
| WO | 2006052374 A2 | 5/2006 |
| WO | 2006109255 A1 | 10/2006 |
| WO | 2006109290 A2 | 10/2006 |
| WO | 2006117772 A1 | 11/2006 |
| WO | 2007089277 A1 | 8/2007 |
| WO | 2007121485 A2 | 10/2007 |
| WO | 2008080149 A1 | 7/2008 |
| WO | 2009140414 A1 | 11/2009 |
| WO | 2009153550 A1 | 12/2009 |
| WO | 2010044988 A1 | 4/2010 |
| WO | 2010068662 A1 | 6/2010 |
| WO | 2010080859 A1 | 7/2010 |
| WO | 2011059913 A1 | 5/2011 |

OTHER PUBLICATIONS

Bretton, Randolph H. et al., "Use of bipolar diathermy to prevent posterior capsule opacification," Journal of Cataract Refractive Surgery 2002; 2 8:866-878.

European Patent Office, Supplementary European Search Report, Application No. EP05810478, Feb. 7, 2008, 2 pgs.

Karmel, Miriam, "Glaucoma Surgies: Trabectome and Canaloplasty Take the Stage," publication, May 2009, pp. 29-30, American Academy of Ophthalmology.

Lewandowski, Julia T., "Improving Ab Interno Trabeculotomy, A combination of advanced technology and insightful design may prompt surgeons to adopt a new technique for lowering IOP," article, Jul. 2007, 4 pages, Bryn Mawr Communications.

International Searching Authority, International Search Report, PCT/US2011/053451, mailed Nov. 14, 2011, 5 pages.

International Searching Authority, Written Opinion, PCT/US2011/053451, mailed Nov. 14, 2011, 7 pages.

International Searching Authority, International Preliminary Report on Patentability, PCT/US2011/053451, dated Apr. 2, 2013, 8 pages.

* cited by examiner

ATTENUATED RF POWER FOR AUTOMATED CAPSULORHEXIS

CROSS-REFERENCE TO RELATED APPLICATION

This application is a continuation of U.S. application Ser. No. 12/893,149, filed Sep. 29, 2010 now U.S. Pat. No. 9,149,388.

TECHNICAL FIELD

The present invention relates generally to the field of cataract surgery and more particularly to methods and apparatus for performing a capsulorhexis.

BACKGROUND

An accepted treatment for cataracts is surgical removal of the lens and replacement of the lens function by an artificial intraocular lens. In the United States, the majority of cataractous lenses are removed by a surgical technique called phacoemulsification. Prior to removing the cataractous lens, an opening, or rhexis, must be made in the anterior capsule. During phacoemulsification, there is a great deal of tension on the cut edges of the anterior capsulorhexis while the lens nucleus is emulsified. Accordingly, a continuous cut or tear (rhexis), without "tags," is a critical step in a safe and effective phacoemulsification procedure.

If the capsule is opened with numerous small capsular tears, the small tags that remain can lead to radial capsular tears which may extend into the posterior capsule. Such a radial tear constitutes a complication since it destabilizes the lens for further cataract removal and safe intraocular lens placement within the lens capsule later in the operation. Further, if the posterior capsule is punctured then the vitreous may gain access to the anterior chamber of the eye. If this happens, the vitreous must be removed by an additional procedure with special instruments. The loss of vitreous is also associated with an increased rate of subsequent retinal detachment and/or infection within the eye. Importantly, these complications are potentially blinding.

Conventional equipment used for phacoemulsification includes an ultrasonically driven handpiece with an attached cutting tip. In some of these handpieces, the operative part is a centrally located, hollow resonating bar or horn directly attached to a set of piezoelectric crystals. The crystals supply ultrasonic vibration for driving both the horn and the attached cutting tip during phacoemulsification.

Many of the known devices and methods used for the capsulorhexis procedure require a great deal of skill on the part of the surgeon to produce a continuous curvilinear capsular opening. This is due to the extreme difficulty in controlling the path of the cutting tip of the device. For example, a typical procedure begins with a capsular incision made with a cystotome, e.g., a cutting tip as described above. This incision is then coaxed into a circular or oval shape by pushing the leading edge of the incision in the capsule, using the cystotome as a wedge rather than in a cutting fashion. Alternatively, the initial capsular incision may be torn into a circular shape by grasping the leading edge with fine caliber forceps and advancing the cut. Either of these approaches involves a very challenging maneuver and the tearing motion can sometimes lead to an undesirable tear of the capsule toward the back of the lens, even in the most experienced hands.

Moreover, even if a smooth capsular opening without tags is ultimately produced, the size and/or position of the capsular opening may present a problem. For instance, a capsular opening that is too small can impede the safe removal of the lens nucleus and cortex and prevent proper intraocular lens insertion into the lens capsule. The additional stresses necessary to accomplish the operation with a small or misplaced capsular opening put the eye at risk for zonular and capsular breakage. Either of these complications will likely increase the length and complexity of the operation and may result in vitreous loss.

A continuous, properly positioned, and circular opening is thus highly desirable because it results in: (1) a significant reduction in radial tears and tags within the anterior capsule, (2) capsule integrity necessary for proper centering of a lens prosthesis; (3) safe and effective hydrodissection; and (4) safe use of capsular procedures on patients having poorly visualized capsules and/or small pupil openings. In addition, the capsulorhexis should be properly dimensioned relative to the diameter of the intraocular lens being implanted in order to reduce the chances of a secondary cataract, also called posterior capsule opacification and for use with proposed accommodative intraocular lens designs. Therefore, there is a continuing need for improved devices for performing anterior chamber capsulorhexis.

Various methods and devices for automating the capsulorhexis process have been proposed. One approach is described in U.S. patent application Ser. No. 12/618,805, filed 16 Nov. 2009 and titled "Capuslarhexis Device Using Pulsed Electric Fields" (hereinafter "the '805 application"). The '805 application, the entire contents of which are incorporated by reference herein, describes methods and apparatus for performing capsulorhexis using high-frequency electrical currents applied to the anterior lens capsule through a unipolar electrode. The device uses pulsed electric fields to perform the cutting action—the pulsed electric field is generated using a ring electrode, placed against the anterior capsule of the eye, and a grounding electrode located at a different position inside or outside the eye. In some embodiments of this system, the ring electrode comprises a thin, electrically conducting wire. A very small cross-section (e.g., less than about 0.25 millimeters in diameter) will yield high-intensity electric fields close to the wire; these electric fields will reduce in intensity further away from the wire. Because a ground electrode having a much larger cross-section than the cutting electrode is used in this system, the electric fields remain attenuated at the grounding electrode, and a high proportion of the available cutting energy is deposited into a thin region immediately around the cutting electrode's wire.

Another system is described in United States Patent Application Publication No. 2006/0100617, the entire contents of which are incorporated herein by reference. This publication describes an autocapsulorhexis device comprising a circular, flexible ring made of an elastomer or an acrylic or thermoplastic material. Embedded within each of various embodiments of this flexible ring is either a resistance-heating element or a pair of bipolar electrodes, which are energized according to known techniques to produce localized heating on the anterior capsule, so as to define a weakened boundary for an easy detachment of the portion of the capsule within the circular ring. Various other devices have been proposed, many of which depend on resistive-heating cautery elements, such as U.S. Pat. No. 6,066,138, issued May 23, 2000; U.S. Pat. No. 4,481,948, issued Nov. 13, 1984; and WIPO Publication No. WO 2006/109290 A2, published Oct. 19, 2006. The entire contents of each of the references identified in this paragraph are incorporated by reference herein, for the purpose of providing background and context for the present invention.

SUMMARY

A capsulorhexis apparatus includes a capsulorhexis probe configured for insertion into an eye through an incision and a pulse generator configured to deliver at least one radio-frequency (RF) pulse to the capsulorhexis probe. The delivered RF pulse has a pre-determined attenuation profile such that the power level of the delivered RF pulse is substantially attenuated over the RF pulse's duration. In some embodiments, the pulse generator is configured to deliver a series of two or more RF pulses to the eye, such that the energy of each of the second and subsequent pulses of the series is substantially attenuated relative to its predecessor.

In some embodiments, the pre-determined attenuation profile is such that the power level of the delivered RF pulse is reduced by at least one-half over the RF pulse's duration. In these and other embodiments, the pre-determined attenuation profile may be designed to ensure that the delivered RF pulse initiates bubble nucleation in the eye, without excessive coalescence or overheating of the lens capsule beyond the targeted area. In several embodiments, a series of two or more RF pulses are delivered to the eye, in such a manner that the energy of each of the second and subsequent pulses of the series is substantially attenuated relative to its predecessor. In some of these embodiments, the amplitude of each of the second and subsequent pulses of the series is substantially attenuated relative to the amplitude of the immediately preceding pulse. In others, the amplitude of each of the second and subsequent pulses is substantially the same as the amplitude of the first pulse of the series, but the length of each of the second and subsequent pulses of the series is substantially shorter than the length of the immediately preceding pulse.

Methods involving the use of intra-pulse attenuation profiles, in which the pulse power is attenuated over the duration of the pulse, or inter-pulse attenuation profiles, in which the energy of each of a series of pulses is attenuated relative to its predecessor, are disclosed. In some embodiments, both techniques are used. Accordingly, one exemplary method for performing capsulorhexis begins with the insertion of a capsulorhexis probe into the anterior chamber of an eye and the positioning of the cutting portion of the capsulorhexis probe in contact with the anterior lens capsule of the eye. At least one radio-frequency (RF) pulse is then delivered to the eye, via the capsulorhexis probe, according to a pre-determined attenuation profile. This profile is such that the power level of the delivered RF pulse is substantially attenuated over the RF pulse's duration.

Another exemplary method also begins with the insertion of a capsulorhexis probe into the anterior chamber of an eye and the positioning of the cutting portion of the capsulorhexis probe in contact with the anterior lens capsule of the eye. A series of two or more radio-frequency (RF) pulses is then delivered to the eye, via the capsulorhexis probe, such that the energy of each of the second and subsequent pulses of the series is substantially attenuated relative to its predecessor. This use of an inter-pulse attenuation profile may be combined with the use of intra-pulse attenuation profiles, in some embodiments.

A capsulorhexis apparatus for implementing the inventive techniques disclosed herein includes, in some embodiments, a capsulorhexis probe configured for insertion into an eye through an incision and a pulse generator electrically connected to capsulorhexis probe. The pulse generator is configured to deliver at least one radio-frequency (RF) pulse to the capsulorhexis probe, such that the delivered RF pulse has a pre-determined attenuation profile such that the power level of the delivered RF pulse is substantially attenuated over the RF pulse's duration. In some embodiments, the pulse generator is instead configured to deliver a series of two or more RF pulses to the eye, such that the energy of each of the second and subsequent pulses of the series is substantially attenuated relative to its predecessor. In still other embodiments, both techniques are used.

Of course, those skilled in the art will appreciate that the present invention is not limited to the above features, advantages, contexts or examples, and will recognize additional features and advantages upon reading the following detailed description and upon viewing the accompanying drawings.

DETAILED DESCRIPTION

As noted above, various methods and devices for automating the capsulorhexis process have been proposed. For instance, the '805 application, incorporated by reference above, describes methods and apparatus for performing capsulorhexis using high-frequency electrical currents applied to the anterior lens capsule through a unipolar electrode. Other capsulorhexis probe configurations are possible, including those that rely on resistance-heating elements or a pair of bipolar electrodes, which are energized according to known techniques to produce localized heating on the anterior capsule. Common to many of these systems is the use of a high-energy pulse generator to deliver calibrated pulse energy to the surgical site.

Although those skilled in the art will appreciate the broader applicability of several of the inventive techniques and apparatus disclosed herein, these techniques will be described with reference to previously disclosed methods for performing capsulorhexis using pulses applied to a heating element placed against the anterior lens capsule. One such method is described in U.S. Patent Application Publication No. 2010/0094278, titled "Capsularhexis Device with Flexible Heating Element, the entire contents of which are incorporated by reference herein. This approach uses a resistive-heating element formed from an electrically resistive, superelastic wire formed into a loop. The heating element is energized with a short pulse or series of pulses of current. The heating of the loop-shaped element sears the lens capsule, effectively creating a smooth continuous cut on the capsule.

In contrast, the system described in the '805 application uses pulsed electric fields to perform the cutting action—the pulsed electric field is generated using a ring electrode, placed against the anterior capsule of the eye, and a grounding electrode located elsewhere, inside or outside the eye. The ring electrode comprises a thin, electrically conducting wire, since a very thin wire will increase cutting efficiency and reduce far-field effects. A very small cross-section (e.g., less than about 0.25 millimeters in diameter) will yield high-intensity electric fields close to the wire; these electric fields will reduce in intensity further away from the wire. Because the ground electrode has a much larger cross-section than the cutting electrode, the electric fields remain attenuated at the grounding electrode. Thus, a high proportion of the available cutting energy is deposited into a thin region immediately around the cutting electrode's wire.

Figure 1:
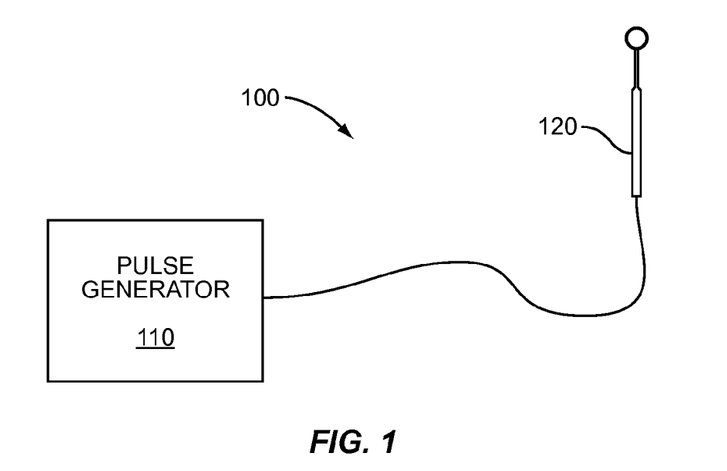
FIG. 1 illustrates a capsulorhexis apparatus according to some embodiments of the invention, including a pulse generator and a cutting electrode device.
Figure 2:
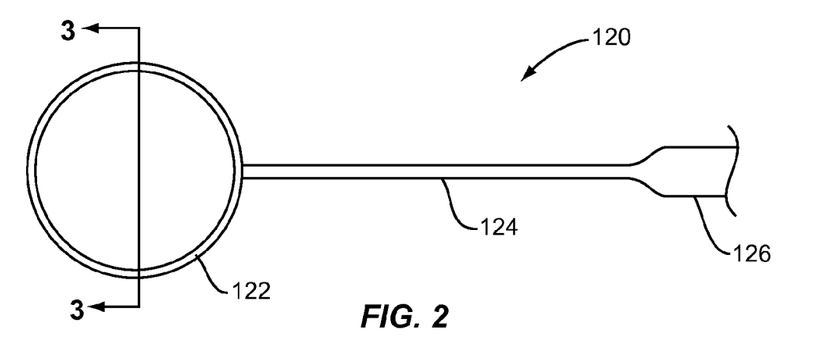
FIG. 2 illustrates details of a capsulorhexis probe.
Figure 3:
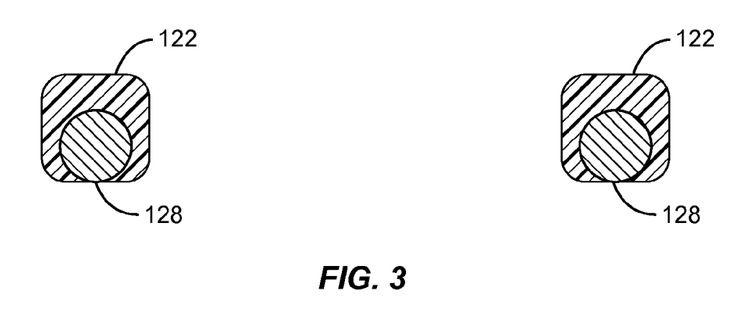
FIG. 3 is a cross-section of the ring portion of the probe of FIG. 2.

FIG. 1 illustrates the components of an exemplary capsulorhexis apparatus according to some embodiments of the invention. The pictured system includes a pulse generator 110, which produces high-frequency pulses for application to the eye through cutting electrode 120. FIGS. 2 and 3 illustrate details of an exemplary cutting electrode device 120. Cutting electrode device 120 includes a flexible ring 122, which a single, ring-shaped, wire electrode 128 embedded therein. A flexible shaft 124 connects the flexible ring 122 to a handle 126. An electrical lead (not shown) runs within shaft 124 and handle 126 to connect electrode 128 to the pulse generator 110. Simpler embodiments may use only a bare wire loop as the heating element.

The flexible ring portion of the apparatus is dimensioned according to the desired size of the capsulotomy, e.g., with a diameter of approximately 5 millimeters. Those skilled in the art will appreciate that a circular opening is preferred, as illustrated in FIG. 2, to avoid tearing when the portion of the lens capsule within the opening is removed. The ring-shaped wire electrode 128 defines the boundaries of the portion of the lens capsule that is subjected to the direct heating that results from the energizing of the electrode.

To reduce collateral damage to the rhexis edge caused by overheating so as to improve rhexis strength and extensibility, attenuated pulses and pulse sequences of radio frequency (RF) voltage may be used to drive the capsulorhexis probes discussed above. As is well known to those skilled in the art, an automated capsulorhexis device is often used in the presence of a viscoelastic material that is introduced to the surgical site to protect the corneal endothelium and maintain the anterior chamber during cataract removal. When the capsulorhexis probe is energized, the resulting heating causes explosive boiling in the viscoelastic material. Boiling may occur in the tissue water, as well. The thermal process in the viscoelastic material closely around the energized probe can be divided into three steps: bubble nucleation at the beginning of the pulse, followed by bubble coalescence, and bubble collapse at the end.

Since a phase change in the viscoelastic material occurs at the nucleation stage, high power is needed to initiate the process. However, once the energized probe element is isolated from the liquid by bubbles, the power needed to maintain a given elevated temperature drops dramatically. This is the result of significantly reduced heat dissipation caused by the low thermal conductivity of the vapor, as compared to the thermal conductivity of the surrounding viscoelastic liquid.

In various embodiments of the invention, then, radio-frequency (RF) pulses delivered to the capsulorhexis probe are attenuated, over each pulse's duration. This intra-pulse attenuation adapts the power output to the rapidly varying power requirements, so as to reduce collateral damage to the rhexis edge caused by overheating. An example of an attenuation profile for an RF pulse is given in FIG. 4. A high voltage at the beginning of the pulse can be used to quickly initiate boiling of the viscoelastic material and tissue water. The pulse amplitude is then attenuated at a pre-determined rate or according to an experimentally determined profile so that the temperature at or near the energized capsulorhexis probe can be maintained at a proper level to produce a through cut in the lens capsule, with less thermal damage to the rhexis edge.

The desired attenuation rates or profiles will depend on several factors, including the characteristics of the applied RF energy, the precise configuration of the capsulorhexis probe or probes, and the like. However, those skilled in the art will appreciate that profiles appropriate to a given physical configuration can be determined experimentally. For instance, the nucleation process induced by various pulse attenuation profiles can be observed to identify attenuation profiles that minimize the coalescence of large bubbles around the energized probe. Likewise, the rhexis itself can be directly observed to determine those profiles that effectively cut the lens capsule without excessive damage, such as damage to the extensibility of the capsule.

Figure 6:
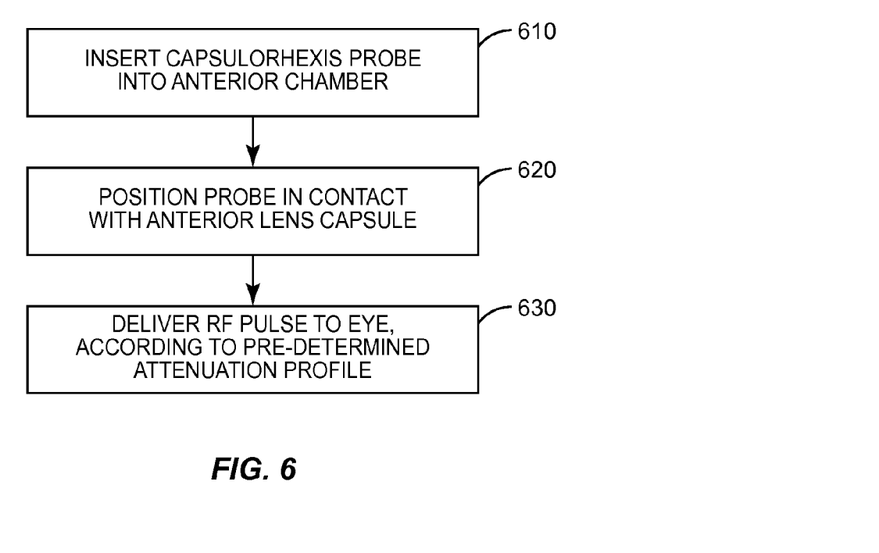
FIG. 6 illustrates a radio-frequency pulse having a pre-determined attenuation profile.

FIG. 6 is a process flow diagram illustrating a method for performing capsulorhexis that exploits the principles discussed above. The process begins, as shown at block 610, with the insertion of a capsulorhexis probe into the anterior chamber, and the positioning of the cutting portion of the probe in contact with the anterior lens capsule of the eye, as shown at block 620. Any of a wide variety of capsulorhexis probe configurations may be used, provided only that the probe is capable of being energized with pulsed RF energy.

As shown at block 630, at least one RF pulse is then delivered to the eye, via the capsularhexis probe. The delivered RF pulse has a pre-determined attenuation profile, such that the power level of the delivered RF pulse is substantially attenuated over the RF pulse's duration. "Substantially attenuated" simply means that the attenuation of power over the course of the pulse is systematic and intentionally induced. Those skilled in the art will appreciate that the generation and delivery of pulsed RF energy to a physical load is inherently imprecise, such that some uncertainties in delivered power and variations in pulse share are unavoidable. In systems employing the intra-pulse attenuation techniques of the present invention, however, the degree of attenuation over an applied pulse exceeds these normal uncertainties and variations.

In some cases, the pre-determined attenuation profile may be such that the power level of the delivered RF pulse is reduced by at least one-half, i.e., 3 dB, over the RF pulse's duration. In others, the degree of attenuation may be far more substantial, e.g., 10, 20, or 30 dB. As discussed above, the particular attenuation profile applied in a given surgical situation may be experimentally determined in advance, and may be designed so that the beginning portion of the delivered RF pulse initiates bubble nucleation in the eye, while the trailing portion is attenuated sufficiently to avoid coalescence of large bubbles and/or to avoid overheating of the lens capsule.

To provide more flexible control of the cutting energy delivered to the surgical site, while further reducing collateral damage caused by thermal denaturation of the tissue, multiple pulses of RF voltage can be used. The duration of these pulses and the timing between them can be designed based on the concept of thermal relaxation time, which is a commonly used parameter for estimating the time required for heat to conduct away from a directly heated tissue region. (For instance, see B. Choi and A. J. Welch, "Analysis of thermal relaxation during laser irradiation of tissue," Las. Surg. Med. 29, 351-359 (2001).) Because it is desirable to keep the heating effects of the capsulorhexis confined to highly localized area, the characteristic thermal relaxation time of the tissue is a useful guide for determining a maximum length of the applied RF pulses, as well as the time between successive pulses, during which the heated viscoelastic and tissue cools.

Figure 4:
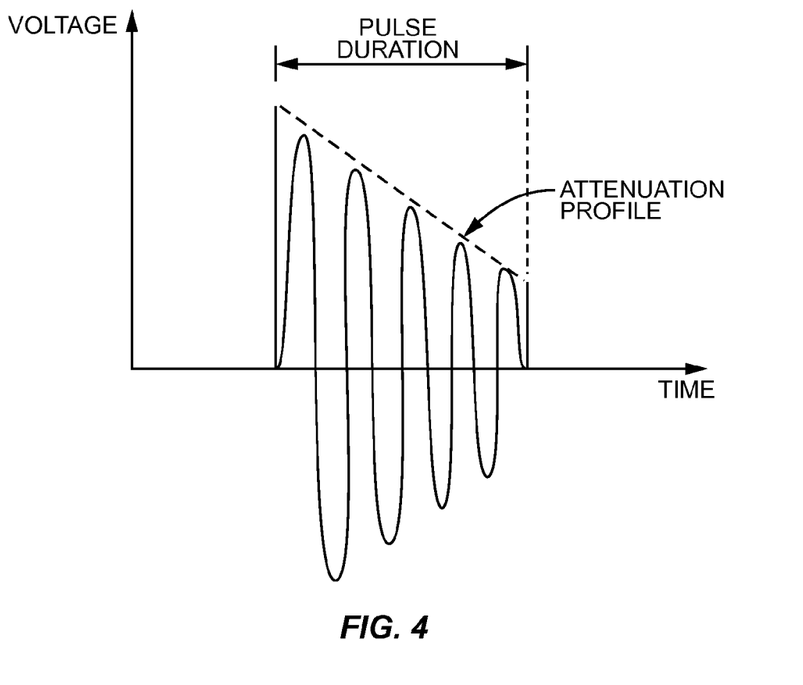
FIG. 4 is a process flow diagram illustrating a method for performing capsulorhexis.
Figure 7:
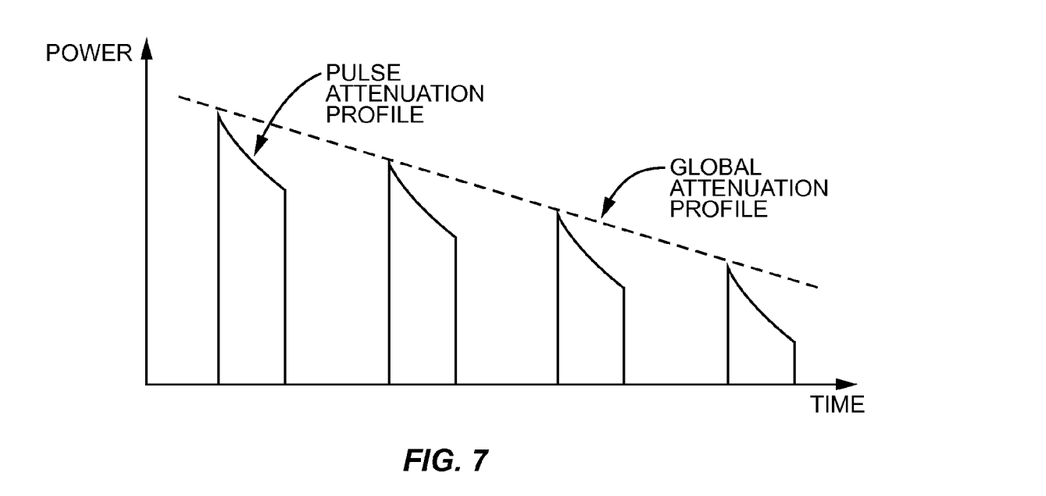
FIG. 7 illustrates a series of progressively attenuated radio-frequency pulses.

Instead of or in addition to the attenuation of the RF voltage within individual pulses, as discussed above in connection with FIGS. 4 and 6, a "global" attenuation profile can be superimposed on the pulse sequence, as illustrated in FIG. 7, to reduce thermal damage caused by accumulation of heat. (FIG. 7 is a power profile of the pulse sequence; FIG. 4, in contrast, plots a voltage profile of a pulse with intra-pulse attenuation.) This global attenuation profile might be regarded as defining "inter-pulse" attenuation, in contrast to the "intra-pulse" attenuation illustrated in FIG. 6. As seen in FIG. 7, each of the second and subsequent pulses in the illustrated sequence is substantially attenuated relative to its predecessor. Thus, the energy of each pulse is reduced, compared to the preceding pulse. As a solely illustrative example, the initial power level of each pulse in the series might be attenuated by twenty percent (about 1 dB) relative to its predecessor, while the power levels during the pulse might also be reduced over the course of the pulse, e.g., by one-half or more. Although the illustrated series of pulses includes only monotonically attenuating pulses, other sequences might include several sub-sequences of pulses, wherein each of the second and subsequent pulses in each sub-sequence is substantially attenuated relative to its predecessor, but the power level is "reset" to a higher level at the beginning of each sub-sequence.

Figure 8:
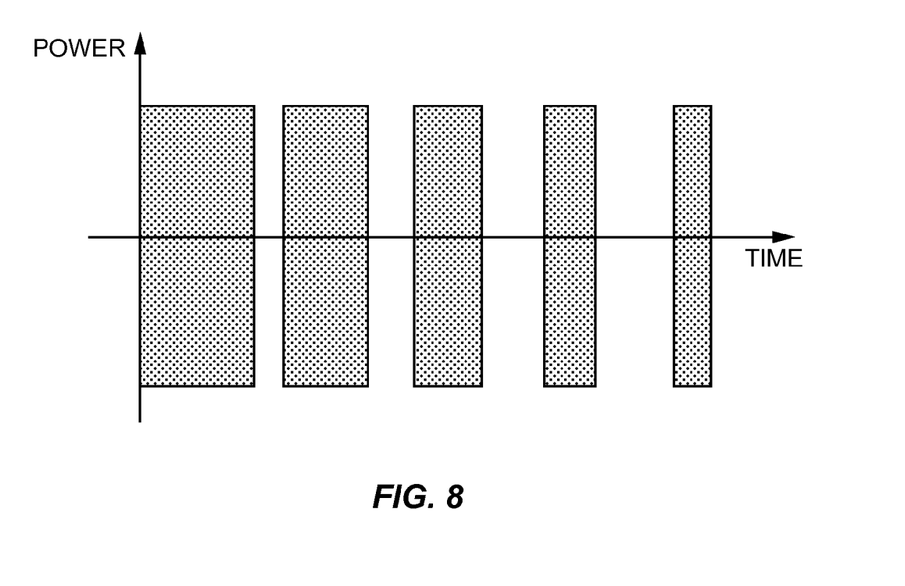
FIG. 8 illustrates a series of attenuated radio-frequency pulses.

FIG. 8 illustrates another way to reduce the energy carried by each of a series of pulses delivered to the eye. In the series of pulses pictured in FIG. 8, the amplitude of each pulse in the series is substantially the same, but the duration of each of the second and subsequent pulses is reduced, relative to the immediately preceding pulse. In addition to the reduced pulse duration, the time between pulses may also be varied, so that the root-mean-square power delivered to the eye over any particular interval attenuates according to a desired profile. Like the technique described in connection with FIG. 7, the technique illustrated in FIG. 8 may be combined with the intra-pulse attenuation profile discussed earlier, so that the amplitude of each of the pulses in the series attenuates over the duration of the pulse.

In some systems, only inter-pulse attenuation or intra-pulse attenuation might be used, while both techniques may be used in others. In addition to the local and global attenuations in the magnitude of RF voltage, varied pulse lengths, duty cycles, etc., can be used to adapt the RF power output even more accurately to the power needs at different stages of the thermal process. Furthermore, the above-mentioned power schemes may be tuned to enhance the role of explosive boiling of tissue water as a cutting mechanism so as to further reduce thermal damage to the rhexis edge. (The lens capsule contains water. If the heating rate is sufficiently high, explosive boiling of water in tissue may occur and this may lead to localized high pressure, i.e., stress to the tissue, due to confinement of the tissue. Such localized stress may play a role in tissue dissecting. Therefore, the cutting mechanism is a combination of thermal and mechanical effects, and collateral damage to the tissue may be reduced compared to pure thermal cutting.)

Figure 5:
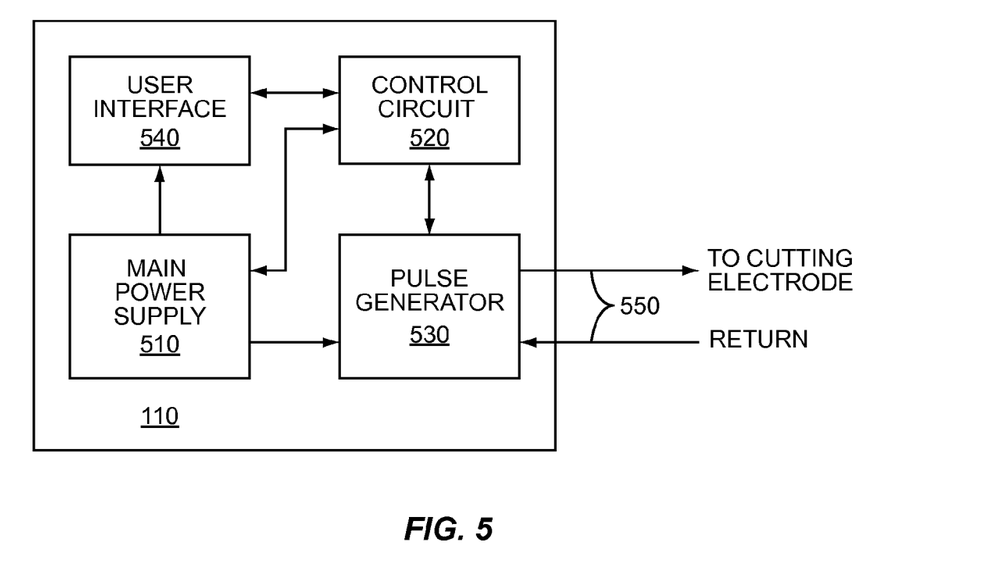
FIG. 5 is a block diagram of a pulse generator.

FIG. 5 illustrates functional elements of a pulse generator 110 according to some embodiments of the present invention. Pulse generator 110 includes a main power supply 510, which may be operated from an external alternating current source (e.g., 120 volts at 60 Hz) or direct current source. Pulse generator 530 generates the RF pulses, from the main power supply 510, under the control of control circuit 520. The RF high-intensity pulses are supplied to the cutting electrode device 120 through leads 550. User interface 540 provides the operator with appropriate mechanisms for operating the pulse generator 110 (e.g., switches, touch-screen inputs, or the like), as well as appropriate feedback (e.g., device status, etc.). Further details of a high-intensity pulsed electric field generator apparatus that can readily be adapted according to the techniques described herein are provided in U.S. Patent Application Publication 2007/0156129 A1, published 5 Jul. 2007, the entire contents of which are incorporated herein by reference.

In some embodiments of the present invention, pulse generator 110 is configured to deliver at least one radio-frequency (RF) pulse to the capsulorhexis probe, wherein the delivered RF pulse has a pre-determined attenuation profile such that the power level of the delivered RF pulse is substantially attenuated over the RF pulse's duration. In other embodiments, the pulse generator 110 is configured to deliver a series of two or more radio-frequency (RF) pulses to the capsulorhexis probe, such that each of the second and subsequent pulses of the series is substantially attenuated relative to its predecessor. Still other embodiments are configured to provide both features, so that both intra-pulse and inter-pulse attenuation profiles are applied to a series of pulses.

The preceding descriptions of various embodiments of capsulorhexis apparatus and methods for utilizing these devices were given for purposes of illustration and example. Those skilled in the art will appreciate, of course, that the present invention may be carried out in other ways than those specifically set forth herein without departing from essential characteristics of the invention. The present embodiments are thus to be considered in all respects as illustrative and not restrictive, and all changes coming within the meaning and equivalency range of the appended claims are intended to be embraced therein.

What is claimed is:

1. A method for performing capsulorhexis, comprising:
   inserting a capsulorhexis probe into the anterior chamber of an eye;
   positioning a portion of the capsulorhexis probe in contact with the anterior lens capsule of the eye; and
   delivering a first radio-frequency (RF) pulse to the eye, via the capsulorhexis probe, wherein the delivered first RF pulse has a pre-determined attenuation profile over a duration of the first RF pulse such that a power level of the delivered first RF pulse is attenuated by at least one-half over the duration of the first RF pulse.

2. The method of claim 1, wherein the attenuation by one-half over the duration of the first RF pulse is such that the power level of the delivered RF pulse is reduced by 3 dB to 30 dB over the duration of the first RF pulse.

3. The method of claim 1, wherein the pre-determined attenuation profile is such that the delivered RF pulse initiates bubble nucleation in the eye.

4. The method of claim 1, further comprising:
   delivering a subsequent RF pulse to the eye, such that a delivered energy of the subsequent RF pulse is attenuated relative to a delivered energy of the first RF pulse.

5. The method of claim 4, wherein a duration of the subsequent RF pulse is less than the duration of the first RF pulse, resulting in the delivered energy of the subsequent RF pulse being less than the delivered energy of the first RF pulse.

6. The method of claim 4, wherein an amplitude of the subsequent RF pulse is substantially the same as an amplitude of the first RF pulse, and wherein a length of the subsequent RF pulse is substantially shorter than a length of the first RF pulse.

7. A method for performing capsulorhexis, comprising:
   inserting a capsulorhexis probe into the anterior chamber of an eye;

positioning a portion of the capsulorhexis probe in contact with the anterior lens capsule of the eye; and delivering a series of two or more radio-frequency (RF) pulses to the eye, via the capsulorhexis probe, such that an energy of each of the second and subsequent pulses of the series is attenuated by at least twenty percent relative to an energy of an immediately preceding pulse, wherein each of the delivered RF pulses of the series has a predetermined attenuation profile such that a power level of each of the delivered RF pulses of the series is attenuated by at least one-half over a duration of the RF pulse.

8. The method of claim 7, wherein an amplitude of each of the second and subsequent RF pulses of the series is attenuated relative to an amplitude of the immediately preceding pulse resulting in the energy of each of the second and subsequent RF pulses of the series to be attenuated by the at least twenty percent relative to the energy of the immediately preceding RF pulse.

9. The method of claim 7, wherein a duration of each of the second and subsequent pulses of the series is shorter than a duration of the immediately preceding RF pulse, resulting in the energy of each of the second and subsequent RF pulses of the series being attenuated by the at least twenty percent relative to its immediately preceding RF pulse.

10. The method of claim 7, wherein an amplitude of the subsequent RF pulse is the same as an amplitude of a first RF pulse.

11. The method of claim 7, further comprising:

delivering a second series of two or more RF pulses to the capsulorhexis probe such that an energy of each of the second and subsequent RF pulses of the second series is attenuated by at least twenty percent relative to an energy of an immediately preceding RF pulse of the second series.

12. The method of claim 9, wherein an amplitude of each of the second and subsequent RF pulses of the series is the same as an amplitude of a first RF pulse of the series.

\* \* \* \* \*